US008688200B2

(12) United States Patent     (10) Patent No.: US 8,688,200 B2
Song et al.     (45) Date of Patent: Apr. 1, 2014

(54) ISCHEMIA DETECTION AND CLASSIFICATION

(75) Inventors: Zhendong Song, Medina, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 338 days.

(21) Appl. No.: 12/915,925

(22) Filed: Oct. 29, 2010

(65) Prior Publication Data

US 2012/0108991 A1     May 3, 2012

(51) Int. Cl.
*A61B 5/04*     (2006.01)

(52) U.S. Cl.
USPC ............................ 600/509; 600/508; 600/512

(58) Field of Classification Search
USPC .......................................... 600/508–509, 512
See application file for complete search history.

(56) References Cited

U.S. PATENT DOCUMENTS

| | | | |
|---|---|---|---|
| 4,374,382 A | 2/1983 | Markowitz | |
| 5,113,869 A | 5/1992 | Nappholz et al. | |
| 5,117,824 A | 6/1992 | Keimel et al. | |
| 5,135,004 A | 8/1992 | Adams et al. | |
| 5,251,621 A | 10/1993 | Collins | |
| 5,313,953 A | 5/1994 | Yomtov et al. | |
| 5,545,186 A | 8/1996 | Olson et al. | |
| 5,755,736 A | 5/1998 | Gillberg et al. | |
| 6,112,116 A | 8/2000 | Fischell et al. | |
| 6,115,630 A | 9/2000 | Stadler et al. | |
| 6,128,526 A | 10/2000 | Stadler et al. | |
| 6,324,421 B1 | 11/2001 | Stadler et al. | |
| 6,381,493 B1 | 4/2002 | Stadler et al. | |
| 6,501,983 B1 | 12/2002 | Natarajan et al. | |
| 6,882,883 B2 | 4/2005 | Condie et al. | |
| 6,937,899 B2 | 8/2005 | Sheldon et al. | |
| 7,066,891 B2 | 6/2006 | Stadler et al. | |
| 7,181,269 B1 | 2/2007 | Kroll | |
| 7,778,698 B1 | 8/2010 | Krishnaswamy et al. | |
| 2003/0149423 A1 | 8/2003 | Fischell et al. | |
| 2004/0122478 A1 | 6/2004 | Stadler et al. | |
| 2004/0215092 A1 | 10/2004 | Fischell et al. | |

(Continued)

FOREIGN PATENT DOCUMENTS

| | | |
|---|---|---|
| EP | 0513457 A1 | 11/1991 |
| WO | 9834537 A1 | 8/1998 |
| WO | 03020367 A1 | 3/2003 |

OTHER PUBLICATIONS

International Search Report and Written Opinion of international application No. PCT/US2011/033811, dated Aug. 19, 2011, 9 pp.

(Continued)

*Primary Examiner* — Nicole F Lavert
(74) *Attorney, Agent, or Firm* — Michael J. Ostrom

(57) ABSTRACT

Techniques for detecting ischemia and classifying a type of ischemia are described. Electrograms of cardiac activity may be generated using implanted or external electrodes, e.g., electrodes carried on vascular leads within the heart and a housing electrode. In some examples, ischemia is detected and classified as benign or malignant based on whether a change an electrogram metric is detected, or first detected, in an endocardial electrogram or a non-endocardial electrogram. The relative timing of the change in the electrogram metric and a change in heart rate or patient activity may also be considered. In some examples, the system may create a stress test for detecting ischemia by instructing the patient to exercise or increasing the cardiac pacing rate.

24 Claims, 10 Drawing Sheets

(56) References Cited

U.S. PATENT DOCUMENTS

| | | |
|---|---|---|
| 2006/0167519 A1 | 7/2006 | Gill et al. |
| 2007/0043393 A1 | 2/2007 | Brockway et al. |
| 2007/0093720 A1 | 4/2007 | Fischell et al. |
| 2007/0129639 A1* | 6/2007 | Zhang et al. .......... 600/509 |
| 2009/0076403 A1 | 3/2009 | Hopenfeld |
| 2009/0082682 A1 | 3/2009 | Fischell et al. |

OTHER PUBLICATIONS

International Preliminary Report on Patentability from international application No. PCT/US2011/033811, dated May 10, 2013, 7 pp.

Hanninen H et al. "ST-segment Level and Slope in Exercise-Induced Myocardial Ischemia with Body Surface Potential Mapping," Am. J. Cardiol. 88:1152-1156 (2001).

Horacek BM et al. "Electrocardiographic ST-Segment Changes during Acute Myocardial Ischemia," Cardiac Electrophysiology Review, vol. 6, No. 3, pp. 196-203 (2002).

Norgaard et al.; "Positional Changes of Spatial QRS- and ST-Segment Variables in Normal Subjects: Implications for Continuous Vectorcardiography Monitoring During Myocardial Ischemia," Journal of Electrocardiology; vol. 33, No. 1; Jan. 2000; pp. 23-30.

U.S. Appl. No. 11/669,357, by Zhendong Song, filed Jan. 31, 2007.

U.S. Appl. No. 11/669,372, by Zhendong Song, filed Jan. 31, 2007.

* cited by examiner

ISCHEMIA DETECTION AND CLASSIFICATION

TECHNICAL FIELD

The invention relates to medical devices, and, more particularly, to medical devices that monitor cardiac health.

BACKGROUND

Like any other organ or tissue structure, the heart requires oxygen and includes coronary arteries to facilitate the delivery of oxygenated blood to cardiac tissue. Unlike other organs, a disruption of the oxygen supplied by the coronary arteries often results in discernable electrical signals. These electrical signals may indicate ischemia or infarct and may also indicate the relative severity of the event.

A standard, 12-lead surface ECG (electrocardiogram) records electrical signals across multiple vectors and produces a highly accurate representation of cardiac data. Each cardiac cycle is distinctly represented. A P-wave is indicative of atrial depolarization, a QRS complex is indicative of ventricular depolarization and a T-wave is indicative of ventricular repolarization. The portion of the signal between the QRS complex and the T-wave is referred to as the ST segment. An elevation of the ST segment from a relative baseline is typically indicative of a complete and sudden coronary occlusion whereas a depression of the ST segment is indicative of another form of ischemia, such as demand ischemia. For example, a coronary artery may be partially occluded, e.g., due to stenosis, allowing sufficient blood flow under normal physiological conditions. When physiological demand increases, such as during exercise, the cardiac tissue is unable to receive sufficient oxygen through the partially occluded arteries, becoming ischemic. Typically, cessation of the activity reduces demand, and as the supply becomes sufficient the ischemia resolves, which resolution is indicated by the ST segment returning to the baseline value.

As indicated, the surface ECG provides accurate and detailed information. In addition, the data is often redundant as each channel that is recorded represents the same events as they occur over different vectors. A physician can therefore check multiple channels when evaluating the data for increased reliability and accuracy.

Implantable medical devices (IMD) often include sensors, e.g., implanted electrodes, that detect electrical cardiac signals. When collected internally, as opposed to on the surface (i.e., ECG), these signals are referred to as an electrogram (EGM). For some vectors, the cathode and anode of a given sensing pair may be relatively close together. For example, a tip electrode and a ring electrode on a common cardiac lead, referred to as a bipolar vector, sense electrical signals across a small portion of the heart. The device housing may include one or more electrodes. Thus, sensing from a unipolar vector, e.g., a tip electrode or coil electrode to the housing ("can") electrode, provides a vector across a greater portion of the heart. These examples relate to implantable pulse generators (IPGs), often referred to as pacemakers or low power devices and implantable cardioverter/defibrillators (ICDs), often referred to as high powered devices, which may also include pacing functionality. IPGs and ICDs typically include a housing implanted subcutaneously or submuscularly and connected to one or more leads that transvenously enter the heart. Other devices, such as an implantable loop recorder (ILR) are implanted subcutaneously to record data, but do not include leads extending to or into the heart.

SUMMARY

Generally, this disclosure describes techniques for detecting ischemia and classifying the type of detected ischemia. Electrodes forming different sensing vectors are used to generate different electrograms of cardiac activity within a patient. In one example, the electrodes may be implanted within the patient. In other examples, one or more electrodes may be surface electrodes external to the patient. Implanted electrodes may be electrodes carried on leads within the heart, electrodes carried on leads outside of the heart but within the patient, or electrodes coupled to the housing of an implantable medical device. Consideration of these different electrograms may facilitate determination of the location and severity of ischemia based on whether and when changes to one or more electrogram metrics, e.g., changes to the ST segment, are detected in the different electrograms.

Two or more electrodes within the heart may be used to monitor an endocardial electrode vector and result in an endocardial electrogram. An endocardial electrogram may be monitored in conjunction within one or more additional, non-endocardial electrograms, which may be produced by monitoring vectors that include at least one electrode that is not located within the heart, e.g., that is not endocardial. Examples of non-endocardial vectors include unipolar vectors, epicardial vectors, or vectors that do not include an electrode on or within the heart. An example of an epicardial vector includes two electrodes located within a coronary vein proximate to the epicardial surface of the left ventricle.

A detected electrogram metric change, e.g., an ST segment change, in an endocardial electrogram may indicate a relatively benign ischemia, e.g., subendocardial ischemia, in the heart. This benign ischemia may be localized to the cardiac tissue near the two electrodes of the endocardial electrode vector. If the heart rate or another indicator of patient activity is elevated during or before the electrogram metric change, the type of ischemia may be classified as a stress induced subendocardial ischemia.

In contrast, non-elevated heart rates or activity during or before changes in the endocardial electrogram, or elevated heart rates or activity after changes in the endocardial electrogram, may indicate that the ST segment changes are due to a transmural ischemia, non-ST elevation myocardial infarction, or another malignant ischemia. Additionally, detected electrogram metric changes, e.g., ST segment elevation, in a non-endocardial electrogram, particularly in the absence of elevated heart rate or activity, may indicate the more severe transmural ischemia, or another malignant ischemia.

Furthermore, when electrogram metric changes are detected via various vectors, e.g., the relative order of detection of electrogram metric changes, may indicate the severity or location of the ischemia. For example, benign or malignant ischemia, e.g., subendocardial or transmural ischemia, may be distinguished based on whether the endocardial or non-endocardial electrogram included, or first included, the electrogram metric changes. Additionally, the relative timing of electrogram metric changes between vectors may indicate the chamber or portion of the heart in which the ischemia is occurring. Upon detection and classification of the type of ischemia, the system may instruct the patient to seek medical attention or notify a healthcare professional of the ischemia to minimize any further damage to cardiac tissue.

Although these techniques to detect and classify ischemia may be used to monitor a patient, these techniques may also be used to perform a stress test on the patient. Since implanted electrodes are used, even low levels of coronary artery occlusion associated with a subendocardial ischemia may be detected. The system may automatically conduct a stress test upon detecting an increased heart rate, or deliver a message to the patient instructing the patient to exercise. If the system includes the ability to pace the patient's heart, the system may alternatively increase the pacing rate to artificially conduct the stress test. After generating endocardial and non-endocardial electrograms from the stress test, the system may be able to identify problem areas of the cardiac vasculature based on any detected ischemia.

In one example, the disclosure describes a method that includes generating a endocardial electrogram of a heart with an endocardial electrode vector within a patient during a time period generating a non-endocardial electrogram of the heart with an epicardial electrode vector during the time period, detecting an ST segment change in at least one of the non-endocardial electrogram or the endocardial electrogram, and automatically classifying an ischemia type for the heart during the time period based on the detection.

In another example, the disclosure describes a system that includes a first electrode and a second electrode both implanted within a heart of a patient, a third electrode outside of the heart, and a processor configured to generate a endocardial electrogram of the heart with an endocardial electrode vector between the first electrode and the second electrode during a time period and generate a non-endocardial electrogram of the heart with an epicardial electrode vector comprising the third electrode during a time period. The system also includes an ischemia detection module configured to detect an ST segment change in at least one of the non-endocardial electrogram or the endocardial electrogram and automatically classify an ischemia type for the heart during the time period based on the detection.

In another example, the disclosure describes a system that includes means for generating a endocardial electrogram of a heart with an endocardial electrode vector within a patient during a time period and generating a non-endocardial electrogram of the heart with an epicardial electrode vector during the time period, means for detecting an ST segment change in at least one of the non-endocardial electrogram or the endocardial electrogram, and means for automatically classifying an ischemia type for the heart during the time period based on the detection.

The details of one or more examples are set forth in the accompanying drawings and the description below. Other features, objects, and advantages will be apparent from the description and drawings, and from the claims.

DETAILED DESCRIPTION

Figure 1:
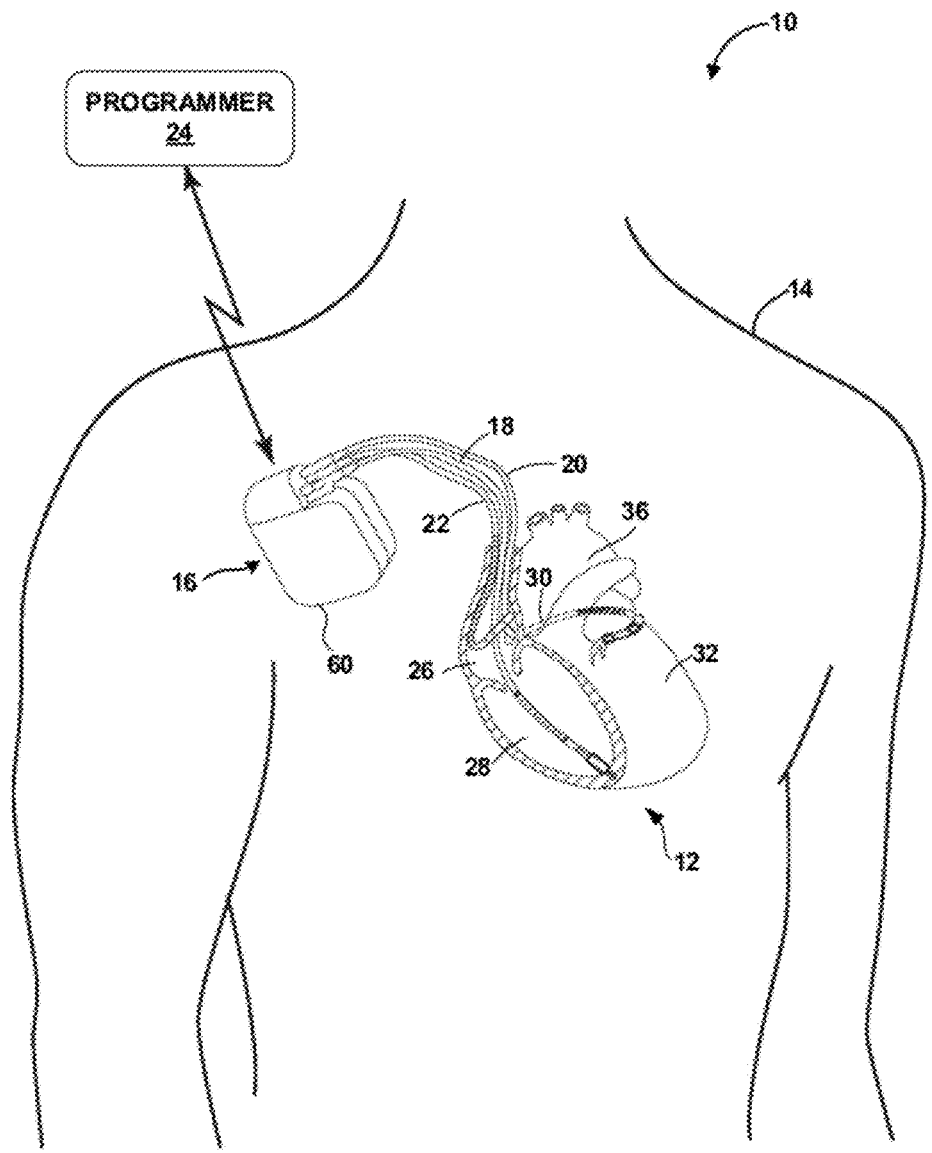
FIG. 1 is a conceptual drawing illustrating an example system configured to detect and classify ischemia that includes an implantable medical device (IMD) coupled to implantable medical leads.

This disclosure generally describes techniques for detecting and classifying ischemia in cardiac tissue. Ischemia, or a restriction in blood supply, may occur due to at least partially occluded coronary blood vessels. Ischemia may be a serious condition because cardiac tissue may become permanently damaged if the blood supply, including oxygen, is reduced. Some types of ischemia are more severe than others and require varying degrees of therapies to minimize cardiac tissue damage.

Subendocardial ischemia is one type of benign ischemia that generally involves a small area in the subendocardial wall of a ventricle, ventricular septum, or papillary muscles. Since the subendocardial area is furthest from the coronary artery blood supply, this area may be the first area to be affected from any reduced blood flow to cardiac tissue. Transmural ischemia is another, more severe, type of ischemia that occurs when substantially the entire thickness of the cardiac muscle loses blood supply, e.g., due to a substantially complete blockage of a coronary artery or other vessel. Transmural ischemia is one example of a malignant ischemia.

Determining the type of ischemia may be important because treatment may be specific to the type of ischemia occurring within the heart. For example, if subendocardial ischemia occurs, the physician may only prescribe a nitrate to relieve the ischemic symptoms. However, more immediate and drastic intervention may be needed for transmural ischemia or other malignant ischemia.

When ischemia occurs, the electrical signals from these affected tissues changes. The techniques and systems described herein detect these changes in electrical signals as changes in one or more features or metrics, referred to herein as metrics, of electrograms of the heart. Implanted electrodes within the heart and outside the heart are used to create different sensing vectors for each electrogram. For example, two or more electrodes within the heart may be used in an endocardial electrode vector to generate an endocardial electrogram. In addition, at least one electrode positioned outside of the heart is used in a non-endocardial electrode vector to generate a non-endocardial electrogram. Whether electrogram metric changes are detected, or the relative timing of electrogram metric changes, in these endocardial and non-endocardial electrograms may indicate different types of ischemia.

In some examples, a non-endocardial electrogram may be generated with one or more external electrodes, i.e., external to the patient and on an external surface, such as skin, of the patient, that form part or all of a non-endocardial electrode vector, e.g., an external electrode used as an anode in a unipolar electrode vector. In one example of this external electrode, a surface electrode may be used to create an electrode vector with a temporary electrode of a lead implanted in the patient during an emergency situation or to augment an ECG stress test. In another example, two surface electrodes may be used to generate a non-endocardial electrogram. These external electrodes may be beneficial in a hospital or clinic environment.

In some examples, temporary implanted electrodes may be used as one or more electrodes in an endocardial or non-endocardial electrogram. For example, a temporary lead may be inserted within the patient to position two electrodes within the heart of the patient. The temporarily implanted electrodes may then be used to generate an endocardial electrogram. Alternatively, an electrode of a temporarily implanted lead may be positioned within the heart and used with a surface electrode or other implanted electrode to generate a non-endocardial electrogram. Temporary leads may be used to provide increased sensitivity for ischemia detection during a stress test or emergency cardiac event, for example.

A non-endocardial electrogram may provide a more global detection of cardiac activity than an endocardial electrogram. While ST segment changes or other electrogram metric changes due to subendocardial ischemia may not be detected in the non-endocardial electrogram at the same time as in the endocardial electrogram (e.g., electrogram metric changes may still occur in the non-endocardial electrogram at a later time than in the endocardial electrogram), transmural ischemia may cause electrogram metric changes that are detectable in the endocardial electrogram. In some examples, ST segment depression in the non-endocardial electrogram and an ST change in the endocardial electrogram may still indicate subendocardial ischemia. In other examples, ST segment elevation in the non-endocardial electrogram and an ST change in the endocardial electrogram may indicate transmural ischemia. Other vectors may also be used to further define ischemic locations or other types of ischemia.

Upon detection and classification of the type of ischemia, the system may perform one or more actions to minimize the effects of the ischemia. For example, the system may instruct the patient to seek medical attention via an external computing device or system alert. Alternatively, or additionally, the system may transmit a notification to a healthcare professional of the type of ischemia that has been detected. This notification may prompt the healthcare professional to contact the patient or simply adjust future medical diagnosis of the patient's condition if the ischemia is minor. In other examples, the system may automatically deliver a therapy, e.g., drug therapy or neural stimulation such as vagal stimulation or spinal cord stimulation, to alleviate the ischemic condition.

Although these techniques to detect and classify ischemia may be used to generally monitor a patient, these techniques may also be used to perform a stress test on the patient. Since implanted electrodes are used, even minor ischemia (e.g., subendocardial ischemia) may be detected for a more accurate coronary artery occlusion status than a surface ECG can produce. The system may automatically conduct a stress test upon detecting an increased heart rate or deliver a message to the patient instructing the patient to exercise. If the system includes the ability to pace the patient's heart, the system may alternatively increase the pacing rate to artificially impose the high oxygen requirements of a stress test. Automatic stress testing may be performed periodically in response to a predetermined schedule or in response to a command from a programmer or remote system, in some examples. After generating endocardial and non-endocardial electrograms from the stress test, the system may be able to identify problem areas of the cardiac vasculature based on any detected ischemia.

The techniques for identifying and classifying ischemia are described herein in the context of detecting ST segment changes. However, other metrics from electrograms or electrocardiograms (e.g., a QRS complex and a T-wave) may be used additionally or instead. Example electrogram metrics that may be used to identify and classify ischemia according to the techniques described herein with respect to ST segment changes include changes in a QRS amplitude, T-wave amplitude, QRS duration, QT interval, corrected QT interval, or a T wave alternans may be used to detect changes indicative of ischemia. In some examples, multiple metrics from an electrogram may be used to more accurately detect or even confirm an ischemia detection or classification.

Although the description herein is generally directed to ischemia in cardiac muscle of a patient, the techniques may also be applied to other organs or tissues within a patient.

FIG. 1 is a conceptual drawing illustrating an example system 10 configured to detect and classify ischemia, and in some cases to provide therapy to heart 12 of patient 14. In the example of FIG. 1, system 10 includes IMD 16, which is coupled to leads 18, 20, and 22, and programmer 24. IMD 16 also includes housing 60. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

Although an implantable medical device and delivery of electrical stimulation to heart 12 are described herein as examples, the techniques for detecting and classifying ischemia of this disclosure may be applicable to other medical devices and/or other therapies. In general, the techniques described in this disclosure may be implemented by any medical device, e.g., implantable or external, that senses a signal indicative of cardiac activity with implanted electrodes. As one alternative example, IMD 16 may be an external cardiac monitor that utilizes implanted electrodes, e.g., percutaneously implanted electrodes, to detect ST segment changes in one or more electrograms.

In the example of FIG. 1, leads 18, 20, 22 extend to the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to leads 18, 20 and 22. Such leads may be used for one or more of cardiac sensing, pacing, or cardioversion/defibrillation. For example, these electrodes may allow alternative electrical sensing configurations that provide improved or supplemental sensing in some patients, e.g. alternative or additional electrograms for ST segment change detection.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for indications of ischemia. IMD 16 may utilize two of any electrodes carried on leads 18 and 22 for an endocardial electrode vector to generate an endocardial electrogram of cardiac activity. If IMD 16 detects ST segment changes in the endocardial electrogram, IMD 16 may classify the ischemia as subendocardial ischemia, or more generally benign ischemia. In addition, IMD 16 may utilize one electrode carried on leads 18, 20, or 22 and the housing electrode (e.g., the can) for a unipolar electrode vector, or two or more electrodes on lead 20 or housing 60 to generate a non-endocardial electrogram of cardiac activity. If IMD 16 also detects ST segment changes in the non-endocardial electrogram in the form of an ST segment elevation, IMD 16 may classify the ischemia as transmural ischemia, or more generally malignant ischemia. Conversely, if IMD 16 does not detect an ST segment change or detects an ST segment change in the form of an ST segment depression within the non-endocardial electrogram, IMD 16 may classify the ischemia as benign or subendocardial ischemia. IMD 16 may use any electrode vectors to detect ST segment changes, but those vectors within or on the heart may be more sensitive to localized ischemia, and those vectors within the heart may be more sensitive to subendocardial ischemia.

IMD 16 may also communicate with external programmer 24. In some examples, programmer 24 comprises a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding any types of ischemia detected during operation. Programmer 24 may provide the dates, times, and type of ischemia detected from ST segment changes in one or more electrograms. Programmer 24 may alternatively deliver one or more alerts regarding detected ischemia as soon as programmer 24 links with IMD 16. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16.

Programmer 24 may also allow the user to define how IMD 16 generates electrograms, detects ST segment or other electrogram metric changes, and classifies ischemic episodes. For example, the user may use programmer 24 to select certain vectors used to generate endocardial and non-endocardial electrograms of heart 12. In addition, the user may set desired thresholds for the magnitude of ST segment or other electrogram metric change that qualifies as detecting ischemia. The user may also determine what types of ischemia are occurring when electrogram metric changes are detected in one or more of the electrograms. In other words, the user may specify what type of ischemia is occurring based upon the electrode vector used for each electrogram. This flexibility for the user may be beneficial when two or more endocardial electrograms are being used to detect and classify different types of ischemia.

In some examples, programmer 24 may also be used in stress testing. When a stress test should take place, programmer 24 may send an instruction to the user, e.g., a clinician or patient 14, for the patient to begin exercising. Programmer 24 may continue this instruction until a target heart rate is reached and/or a predetermined time period has elapsed. During this period of exercise, IMD 16 may monitor one or more electrograms for ST segment changes indicative of ischemia. If IMD 16 detects any ischemia during the stress test, IMD 16 may transmit such detection to programmer 24 so that programmer 24 may present the classified type of detected ischemia to the user. In examples in which IMD 16 begins an automated stress test by increasing the pacing rate for heart 12, programmer 24 may notify the user when the increased pacing has started for the stress test. In an automated stress test, patient 14 may not need to exercise since IMD 16 is artificially raising cardiac demand. Example techniques for forced stress tests are described in U.S. Pat. No. 6,882,883 to Condie et al., which issued on Apr. 19, 2005 and is entitled, "IMPLANTABLE MEDICAL DEVICE (IMD) SYSTEM CONFIGURABLE TO SUBJECT A PATIENT TO A STRESS TEST AND TO DETECT MYOCARDIAL ISCHEMIA WITHIN THE PATIENT," and is incorporated herein by reference in its entirety.

Generally, atrial pacing may be used to perform an automated stress test with IMD 16 to keep the intrinsic QRS complex intact and maintain easier detection of ischemia. However, other pacing methods may also be used, e.g., ventricular pacing. An example method for measuring ST segment changes during ventricular pacing is described in U.S. Pat. No. 6,381,493 to Stadler et al., which issued on Apr. 30, 2002 and is entitled, "ISCHEMIA DETECTION DURING NON-STANDARD CARDIAC EXCITATION PATTERNS," and is incorporated herein by reference in its entirety.

Alternatively, the healthcare professional may instruct IMD 16 to conduct a stress test and look for ischemia whenever the heart rate of patient 14 exceeds a test threshold. For example, the user may determine that IMD 16 shall monitor endocardial and non-endocardial electrograms for ST segment changes any time that the heart rate exceeds 120 beats per minute. IMD 16 may therefore continue to monitor the evolving health of cardiac vasculature within patient 14.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2A:
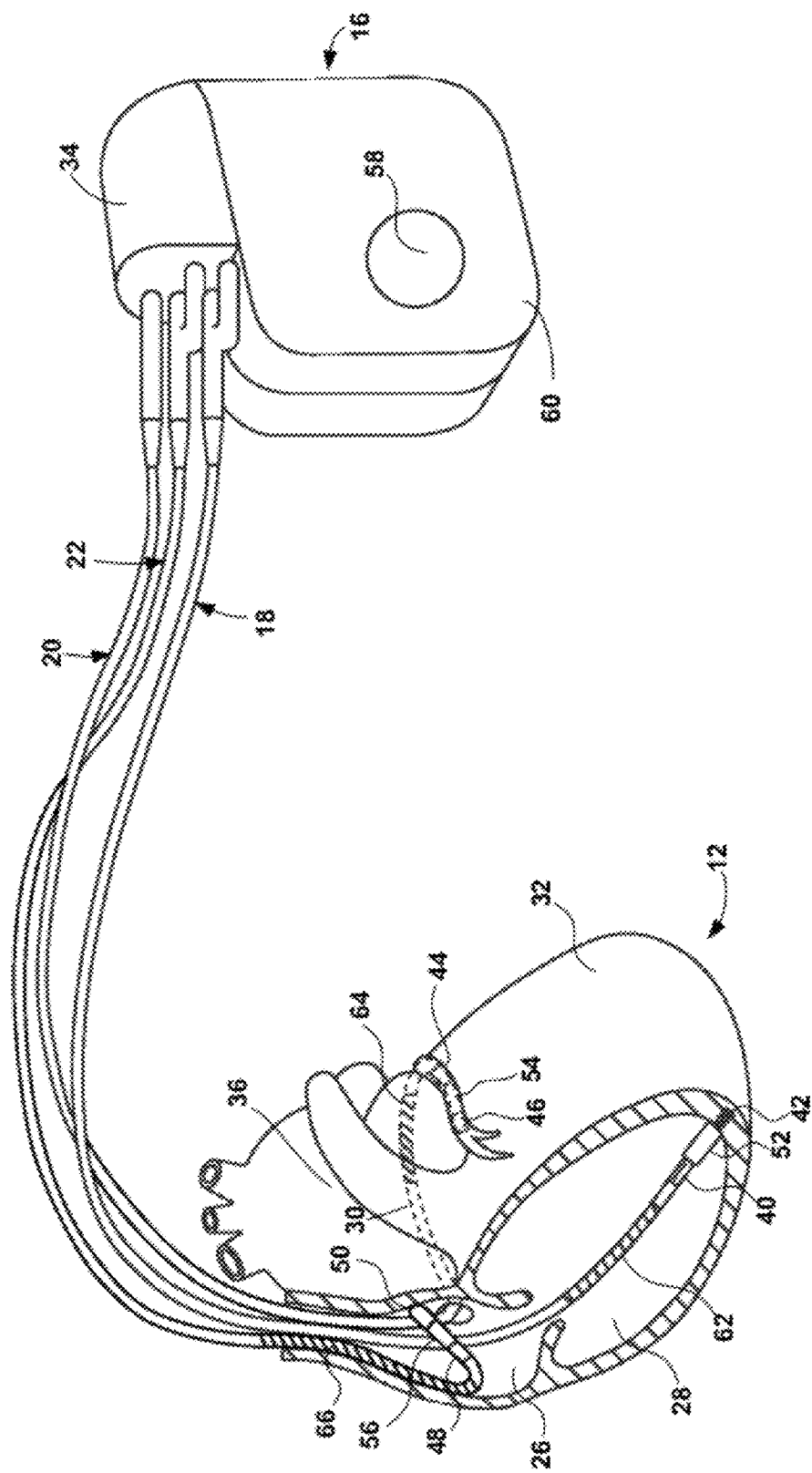
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12. In this manner, housing electrode 58, or multiple housing electrodes, may be used to generate non-endocardial electrograms in some examples.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12.

Figure 2B:
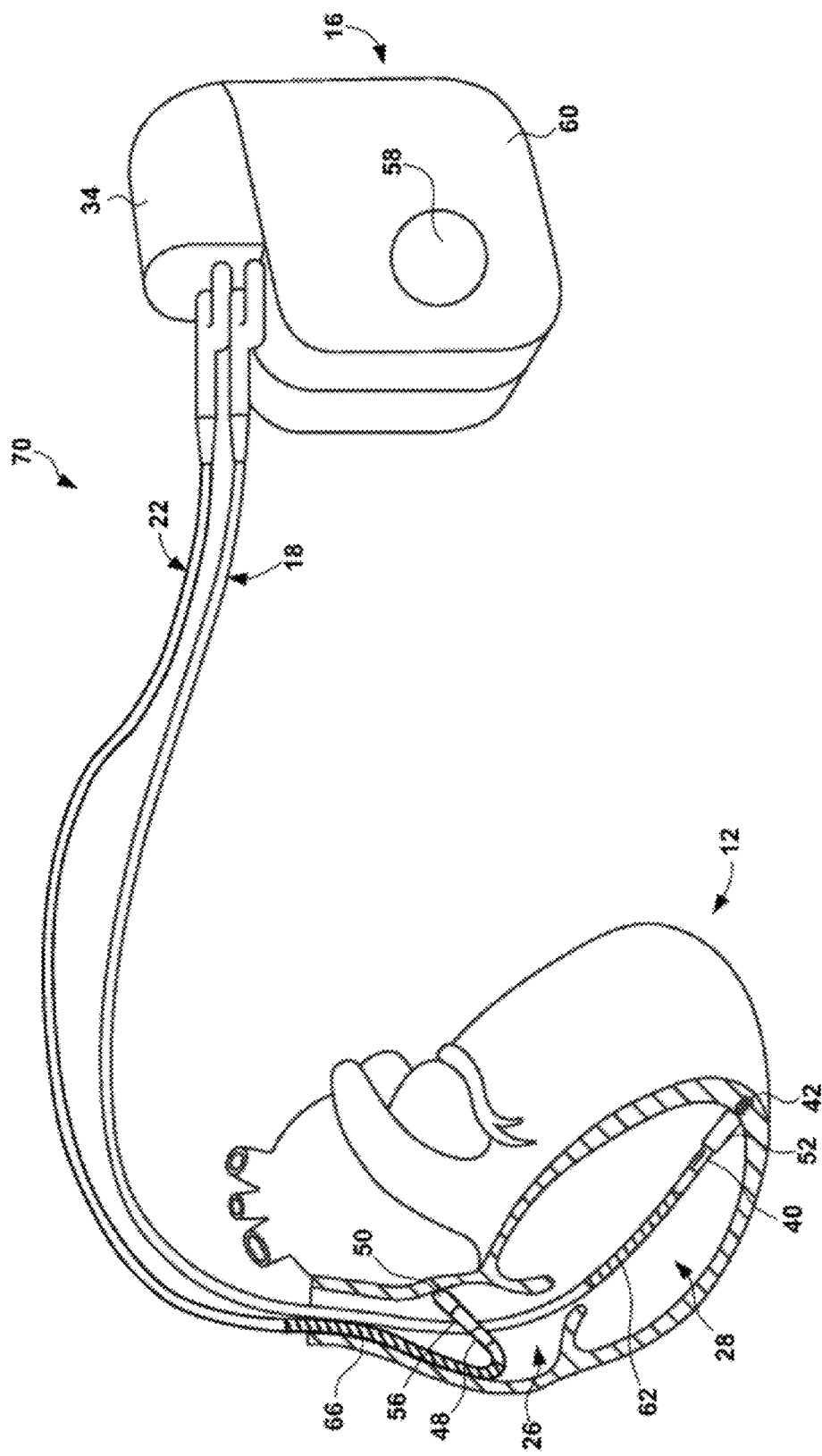
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2A, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of this type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to generate electrograms of heart 12 and detect ST segment changes indicative of various types of ischemia. Electrodes 40, 42, 48, 50, 62, and 66 may be considered endocardial electrodes because they are within heart 12 or in contact with cardiac tissue, and two endocardial electrodes may create an endocardial electrode vector. Generally, endocardial electrode vectors are bipolar electrode pairs, e.g., a small bipole. Electrodes 44, 46, and 64 may be considered epicardial, or non-endocardial, electrodes because each of these electrodes reside outside of heart 12 within coronary sinus 30. Each of electrodes 44, 46, and 64 may be used in unipolar electrode combinations, for example, for a non-endocardial electrogram.

In one example, the endocardial electrode vector may be created with tip electrode 42 at the distal end of lead 18 and ring electrode 40 proximal to electrode 42 on RV lead 18. The endocardial electrogram, e.g., an endocardial electrogram, generated from electrodes 40 and 42 may be sensitive to electrical activity occurring within cardiac muscle around the right and left ventricle. Indeed, tip electrode 42 is contacts cardiac tissue actually implanted within the cardiac tissue of right ventricle 28. This sensitivity may allow IMD 16 to detect ST segment changes in the endocardial electrogram representative of subendocardial ischemia. In other examples, an endocardial electrogram may be created from endocardial electrode vectors using electrodes 48 and 50 or other electrode pairs in which both electrodes are within the heart. Each electrode vector would be sensitive to cardiac tissue, and particularly subendocardial tissue, adjacent to the electrodes of the electrode vector. A clinician or the IMD 16 may select which endocardial electrode vectors to use when generating the endocardial electrograms based upon patient history or other patient risk factors. Furthermore, IMD 16 may generate multiple endocardial electrograms with several different endocardial electrode vectors in other examples.

Housing electrode 58, or another electrode implanted outside of heart 12, may be combined with an endocardial electrode to create a unipolar electrode vector, which is an example of a non-endocardial electrode vector. In other examples, the non-endocardial vector may be created with two implanted electrodes outside of heart 12.

In one example, the non-endocardial electrode vector may include housing electrode 58 and tip electrode 42. The non-endocardial electrogram generated by this electrode vector may be more representative of cardiac activity of the heart as a whole. In other words, ST segment changes in the non-endocardial electrogram may be indicative of transmural ischemia because a larger portion of cardiac muscle has been affected by the loss of blood flow. Since IMD 16 may analyze ST segment changes in both endocardial and non-endocardial electrograms (simultaneously or non-simultaneously), ST segment changes detected in both endocardial and non-endocardial electrograms may lead to a classification that transmural ischemia has occurred when the ST segment change in the non-endocardial electrogram is an elevation. If ST segment changes in the non-endocardial electrogram are ST segment depression, then subendocardial ischemia may be detected. In other examples, the non-endocardial electrode vector may include other combinations of electrodes, e.g., one electrode within heart 12 and one electrode outside of heart 12 or both electrodes implanted outside of heart 12. Although endocardial electrode vectors and non-endocardial electrode vectors may use a common electrode, electrodes may be exclusive to each vector.

FIG. 2B is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection and classification of ischemia according to this disclosure may be performed in two lead systems in the manner described herein with respect to three lead systems. In other examples, a system similar to systems 10 and 70 may only include one lead (e.g., any of leads 18, 20 or 22) to detect and classify ischemia via ST segment changes. As long as the system can generate endocardial and non-endocardial electrograms of heart 12, the system may be capable of detecting and classifying different types of ischemia within cardiac tissue.

Figure 3:
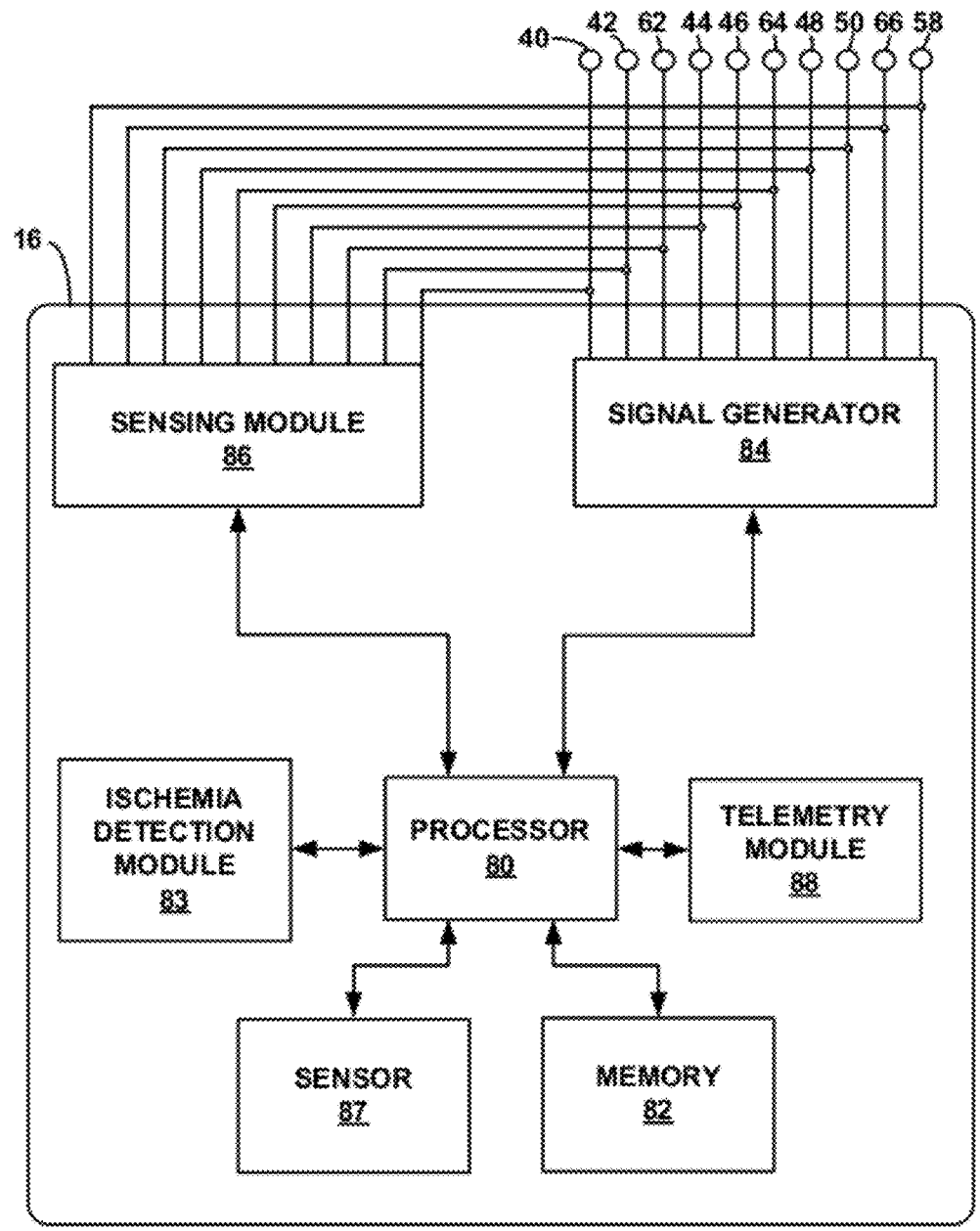
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, ischemia detection module 83, signal generator 84, sensing module 86, sensor 87, and telemetry module 88. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing may be done to determine heart rates, arrhythmias, or detect ST segment changes due to ischemia. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat.

No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as VF or VT. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects ventricular tachycardia when the interval length falls below 360 milliseconds (ms) and fibrillation when the interval length falls below 320 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. In the event that processor 80 detects an atrial or ventricular tachyarrhythmia based on signals from sensing module 86, and a cardioversion or defibrillation shock is desired, processor 80 may control the amplitude, form and timing of the shock delivered by signal generator 84.

Processor 80 may also generate electrograms from two or more electrode vectors of any combination of electrodes 40, 42, 44, 46, 48, 50, 58, 62, 64, and 66 for the purpose of detecting types of ischemia from ST segment changes. For example, processor 80 may generate an endocardial electrogram of heart 12 with an endocardial electrode vector between electrodes 40 and 42 and generate a non-endocardial electrogram of heart 12 with a non-endocardial electrode vector between electrode 42 and housing electrode 58. Processor 80 may generate the electrograms during a particular time period. The time period may be a rolling time period to stay current with patient 14 condition or a specific time period during an hour, day, week, or month. In some examples, the time period may be the period in which stress testing is performed. In other examples, sensing module 86 or ischemia detection module 83 may generate one or more of the electrograms.

Ischemia detection module 83 may analyze the endocardial and non-endocardial electrograms to detect ST segment changes in any of the electrograms. Ischemia detection module 83 may receive the electrograms, or representative data, directly from processor 80 and sensing module 86 or memory 82. In other examples, ischemia detection module 83 may receive analog or digital electrograms from sensing module 86. It is noted that functions attributed to ischemia detection module 83 herein may be embodied as software, firmware, hardware or any combination thereof, and may be a software module or process implemented by processor 80.

From each electrogram, ischemia detection module 83 may detect ST segment changes when they occur within the electrograms. As stated above, these ST segment changes may be an elevation or depression in the segments that occur because of ischemia in the cardiac muscle of heart 12. Depending upon the electrogram in which the ST segment change was detected, ischemia detection module 83 may classify the type of ischemia. For example, ischemia detection module 83 may automatically classify the ischemia type as benign ischemia, e.g., subendocardial ischemia, when ST segment changes are detected in an endocardial electrogram, and in some cases, an ST segment depression or no ST segment change is detected in the non-endocardial electrogram. However, ischemia detection module 83 may automatically classify the ischemia type as malignant ischemia, e.g., transmural ischemia, when ST segment changes are detected, or also detected, in a non-endocardial electrogram. More specifically, ST segment elevation in the non-endocardial electrogram may indicate transmural ischemia. In some cases, ST segment depression in the non-endocardial electrogram may indicate subendocardial ischemia. The ST segment changes may include magnitude changes between ST segments and/or changes in the relative timing of the changes in the ST segments. In this manner, monitoring electrograms from different electrode vectors may allow ischemia detection module 83 to classify the type of ischemia that has occurred within patient 14. This ischemia type may be beneficial to provide the appropriate therapy to patient 14.

In addition to detecting ST segment changes in the electrograms, ischemia detection module 83 may also calculate a heart rate, e.g., the R-R interval between cardiac cycles, from the electrograms or based on indications from sense amplifiers within sensing module 86. Alternatively, ischemia detection module 83 may retrieve the already determined heart rate corresponding to the electrogram time period from processor 80 or memory 82. Ischemia detection module 83 may use the heart rate information to aid in classifying the type of ischemia.

For example, ischemia detection module 83 may classify the ischemia type as stress induced subendocardial ischemia when ST segment changes are detected in the subendocardial electrogram and there has been a substantial increase in patient heart rate preceding and/or during the same time period as the ST segment changes. In some examples, a heart rate increase after ST segment change detection may indicate that a malignant ischemia is present because increasing heart rates after an ischemic insult generally indicates a worse prognosis for patient 14. Based on the timing of the heart rate change in relation to detected ischemia, IMD 16 may recognize the severity of the ischemic condition.

A substantial increase in heart rate may indicate increased oxygen demand by heart 12. The substantial increase may be defined by a predetermined elevated threshold, a predetermined beat per minute increment over patient 14 resting heart rate, or a percentage increase over patient 14 resting heart rate. In some examples, ischemia detection module 83 may classify the ischemia type as non-ST elevation myocardial infarction when ST segment changes have been detected in the subendocardial electrogram and the heart rate had stayed substantially constant during the ST segment change or had elevated following the detection of the ST segment change. A non-ST elevation myocardial infarction may require urgent medical attention because it indicates a larger occlusion of the coronary arteries. In addition, detection of a heart rate increase following detected ST segment changes may be even more urgent and require medical attention as soon as possible.

Similarly, ischemia detection module 83 may utilize detected patient activity levels in addition to, or in the alternative, to aid in classifying the type of ischemia. As illustrated in FIG. 3, IMD 16 may include a sensor 87. Sensor 87 may include a patient activity sensor, e.g., body movement sensor, such as an accelerometer, strain gauge, mercury switch, or piezoelectric element. In some examples, sensor 87 may additionally or alternatively sense the pressure of blood or other bodily fluids of patient. In some examples, ischemia detection module 83 may detect patient respiration based on an impedance or other signal received from the electrodes coupled to IMD 16 via sensing module 86. In general, ischemia detection module 83 may receive one or more signals indicating heart rate, patient activity, respiration, or other indicators of patient demand for oxygen from sensing module 86 or sensor 87.

Ischemia detection module 83 may use the patient activity or other demand signals to determine the timing of increased activity or demand relative to electrogram metric, e.g., ST segment, changes, in the same or a similar manner described above with respect to heart rate. In patients with chronotropic incompetence, for example, an activity level or respiration rate may be a preferred indication of stress because, in such patients, heart rate does not change due to activity and stress.

IMD 16 may also be configured to conduct stress testing so that ischemic episodes can be detected and used to identify possible stenosis within one or more coronary arteries. In one example, processor 80 may automatically initiate stress testing when an increase in heart rate is detected. Initiating stress testing may include instructing ischemia detection module 83 to monitor electrograms for ischemia by detecting ST segment changes when they occur. In another example, processor 80 may generate an instruction for delivery to patient 14 via telemetry module 88 to be presented to patient 14 by programmer 24 or another external computing device. The instruction may tell patient 14 to being exercising so that a stress test can be completed. Processor 80 may also instruct patient 14 when exercise may cease because the stress test is completed.

In other examples, patient 14 may not need to exercise for the stress test to occur. Processor 80 may increase the pacing rate to artificially induce an increase in heart rate that demands more blood flow to heart 12. Processor 80 may transmit an alert to patient 14 when the increase in pacing rate occurs so that patient 14 may not be caught off guard by an unwarranted increase in heart rate. In this manner, patient 14 may elect to postpone the stress test if it would be disruptive to the current activities of patient 14.

In some examples, ischemia detection module 83 may be incorporated into processor 80 or sensing module 86. In any case, ischemia detection module 83 may detect and classify types of ischemia based upon the detected ST segment changes. Ischemia detection module 83 may use predetermined criteria to determine when an ST segment change has been detected. For example, these criteria may include a predetermined threshold. The predetermined threshold may be a percentage of a QRS complex amplitude, a voltage threshold, or a variability of the ST segment. For example, techniques for ischemic detection from implanted devices are described in U.S. Pat. No. 6,128,526 to Stadler et al., which issued on Oct. 3, 2000 and is entitled, "METHOD FOR ISCHEMIA DETECTION AND APPARATUS FOR USING SAME," and is incorporated herein by reference in its entirety.

In the example of a percentage of a QRS complex amplitude being used as the predetermined threshold, ischemia detection module 83 may detect, or identify, a change in the ST segment when the amplitude of the ST segment exceeds a percentage of the amplitude of the previous QRS complex. The value of the predetermined threshold percentage may be set between approximately 5 percent and 50 percent. Example threshold percentages may be approximately 10 percent or 20 percent. In some examples, the ST segment amplitude may be averaged over a period of time, e.g., a rolling average, and the QRS complex amplitude may be likewise averaged over the same period of time.

In the example of a voltage threshold, the predetermined threshold may be set to a voltage change over normal ST segments. If ischemia detection module 83 detects that the ST segment amplitude as exceeded the voltage threshold, ischemia will be reported. The voltage threshold may be set between approximately 0.05 millivolts (mV) and 5 mV. Example voltage thresholds may be approximately 1.0 mV or 0.1 mV. Similar to the percentage of QRS amplitude, the voltage of the ST segment may be averaged over a period of time, e.g., a rolling average, before being compared to the voltage threshold. In other examples, the voltage threshold may be an absolute voltage ceiling or floor, in either the positive or negative direction, for the ST segment amplitude that indicates ischemia.

Alternatively, the ST segment change may be detected upon a variability of the ST segment. Once the ST segment deviation over a period of time has reached a threshold relative to the previously observed variability of the ST segment deviation, ischemia detection module 83 may detect that ischemia is present in the electrogram. In any event, ischemia detection module 83 may implement a scheme to prevent trivial changes in ST segments from indicating the presence of ischemia.

In any example of the predetermined threshold, the threshold may change over time or to best fit the condition of patient 14. For example, the user may adjust the threshold to eliminate false positive or false negative ischemia detections. Alternatively, processor 80 may automatically adjust the predetermined threshold if certain conditions are present in patient 14. For example, the threshold may be adjusted if patient 14 is experiencing certain arrhythmias or the normal patient 14 electrograms change in some manner.

In some examples, processor 80 may provide an alert to a user, e.g., of programmer 24, regarding any detected type of ischemia via telemetry module 88. Additionally or alternatively, processor 80 may suggest a course of therapy or instruct patient 14 to seek medical attention. These alerts and notifications may be dependent upon the type of ischemia classified by ischemia detection module 83. For example, transmural ischemia detection may prompt processor 80 to instruct patient 14 to seek medical attention. However, sub-endocardial ischemia detection may prompt processor 80 to alert patient 14 of the occurrence or even just note the detection in memory 82 for review by a clinician at a later time. Alternatively, processor 80 may provide an electrogram (EGM) or other sensed signal to an external device, e.g., programmer 24, via telemetry module 88 for further evaluation of ST segment changes or other ischemia related analysis. Alternatively, IMD 16 may directly indicate to patient 14 that medical treatment is needed due to ischemia detection. IMD 16 may include a speaker to emit an audible sound through the skin of patient 14 or a vibration module that vibrates to notify patient 14 of needed medical attention.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

In some embodiments, IMD 16 may automatically provide therapy to patient 14 when one or more types of ischemia are detected. For example, IMD 16 or another device may include a drug pump that delivers a dose of medication to alleviate the ischemia conditions. This drug pump may be in addition to or in place of electrical stimulation therapy devices.

Figure 4:
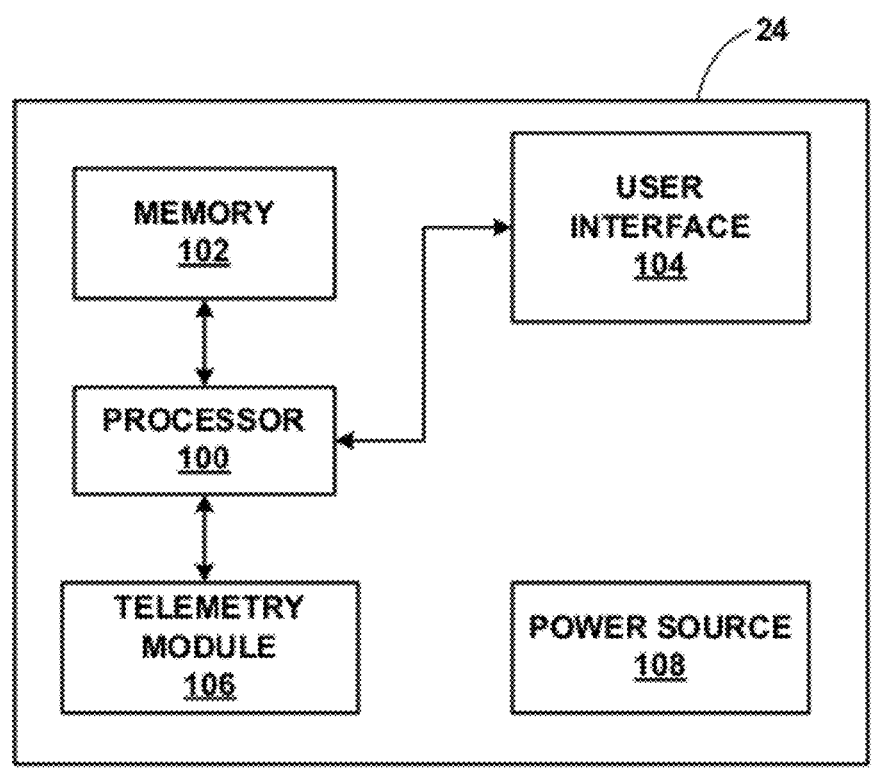
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the type of detected ischemia via programmer 24.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may receive an alert or notification of detected ischemia from telemetry module 88 of IMD 16. The alert or notification may be automatically transmitted based on the ischemia type. In addition, the alert may be a notification to a healthcare professional, e.g., a clinician or nurse, of the ischemia type detected and/or an instruction to patient 14 to seek medical treatment for the detected ischemia. In response to receiving the alert, user interface 104 may present the notification to the healthcare professional regarding the detected ischemia type or present an instruction to patient 14 to seek medical treatment.

Upon receiving the alert via user interface 104, the user may also interact with user interface 104 to cancel the alert, forward the alert, retrieve data regarding the detected ischemia (e.g., ST segment changes or a portion of the electrogram), modify the predetermined threshold used to detect ST segment changes, or conduct any other action related to the treatment of patient 14. In some examples, the clinician may be able to review electrogram data to diagnose any other problems with patient 14. User interface 104 may even suggest treatment along with the alert, e.g., certain drugs and doses, to minimize symptoms and tissue damage that could result from the ischemia. User interface 104 may also allow the user to specify the type and timing of alerts based upon the type of ischemia classified by IMD 16.

Programmer 24 may also be used for stress testing. For example, processor 80 of IMD 16 may generate an instruction for patient 14 to increase heart rate via exercise, and user interface 104 may present the instruction to patient 14. Patient 14 may interact with user interface 104 to accept the exercise instruction, indicate when exercising has begun, or to postpone the stress test to a later time. Alternatively, processor 80 may automatically begin a stress test by increasing the pacing rate of heart 12 to artificially increase the heart rate. User interface 104 may notify patient 14 when the stress test is to begin so that patient 14 will not be alarmed at the increase in heart rate. In some examples, patient 14 may be able to interact with user interface 104 to accept the processor initiated stress test or postpone the stress test. Patient 14 may then retain avoid undesirable conflicts between patient activities and the stress test.

In some examples, processor 100 of programmer 24 and/or one or more processors of one or more networked computers may perform all or a portion of the techniques described herein with respect to processor 80 and IMD 16. For example, processor 100 or an ischemia detection module within programmer 24 may analyze electrograms to detect ST segment changes and/or classify the type of ischemia based on the endocardial or non-endocardial electrograms.

Figure 5:
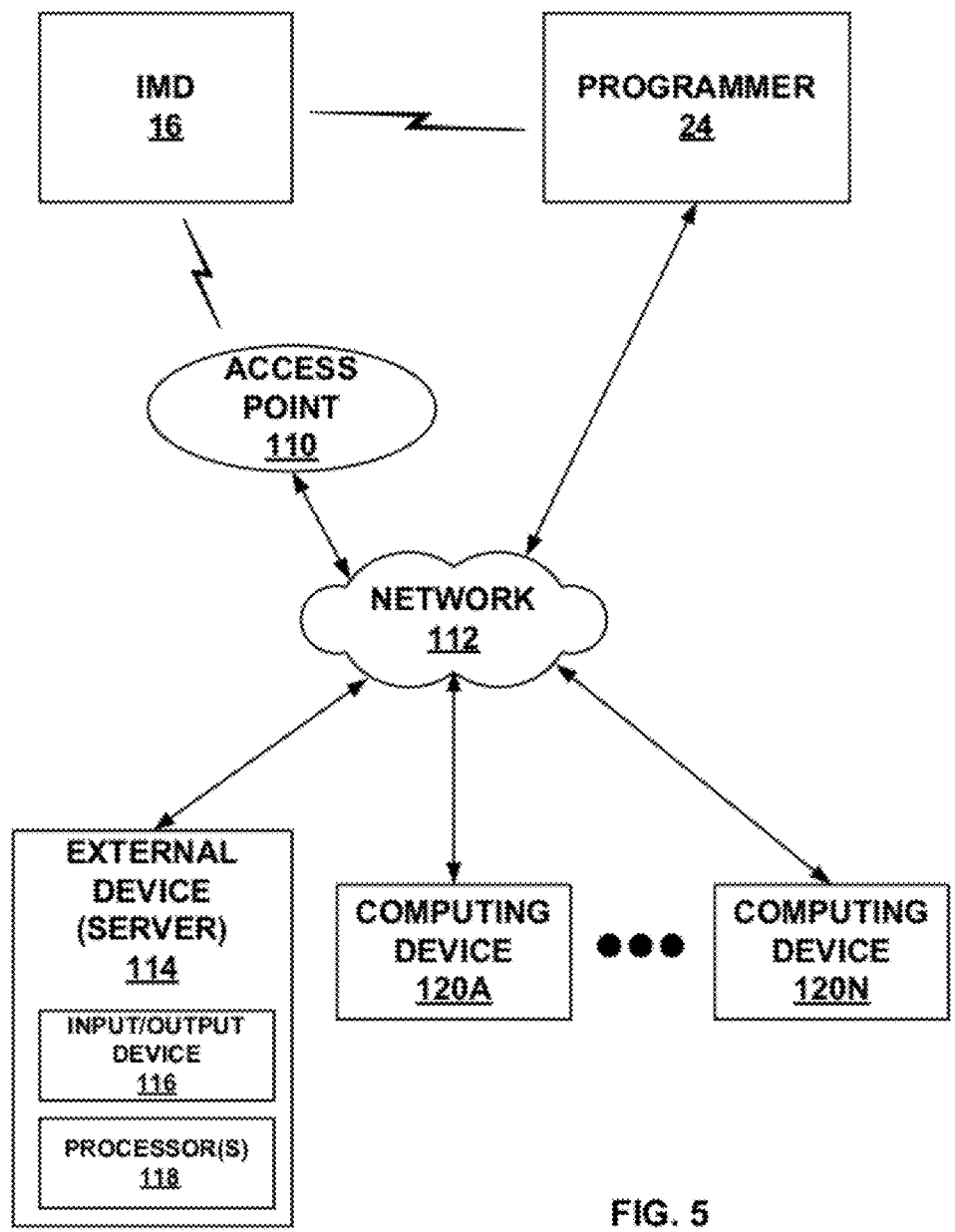
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 204, and one or more computing devices 210A-210N, that are coupled to the IMD 16 and programmer 24 shown in FIG. 1 via a network 112. In this example, IMD 16 may use its telemetry module 88 to communicate with programmer 24 via a first wireless connection, and to communication with an access point 110 via a second wireless connection. In the example of FIG. 5, access point 110, programmer 24, server 114, and computing devices 120A-120N are interconnected, and able to communicate with each other, through network 112. In some cases, one or more of access point 110, programmer 24, server 114, and computing devices 120A-120N may be coupled to network 112 through one or more wireless connections. IMD 16, programmer 24, server 114, and computing devices 120A-120N may each comprise one or more processors, such as one or more microprocessors, DSPs, ASICs, FPGAs, programmable logic circuitry, or the like, that may perform various functions and operations, such as those described herein.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, server 114 or computing devices 120 may control or perform any of the various functions or operations described herein, e.g., detect and/or classify types of ischemia from ST segment changes in electrograms or other data received from IMD 16 or control detection and classification of ischemia by IMD 16.

In some cases, server 114 may be configured to provide a secure storage site for archival of sensing integrity information that has been collected from IMD 16 and/or programmer 24. Network 112 may comprise a local area network, wide area network, or global network, such as the Internet. In some cases, programmer 24 or server 114 may assemble sensing integrity information in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

Figure 6:
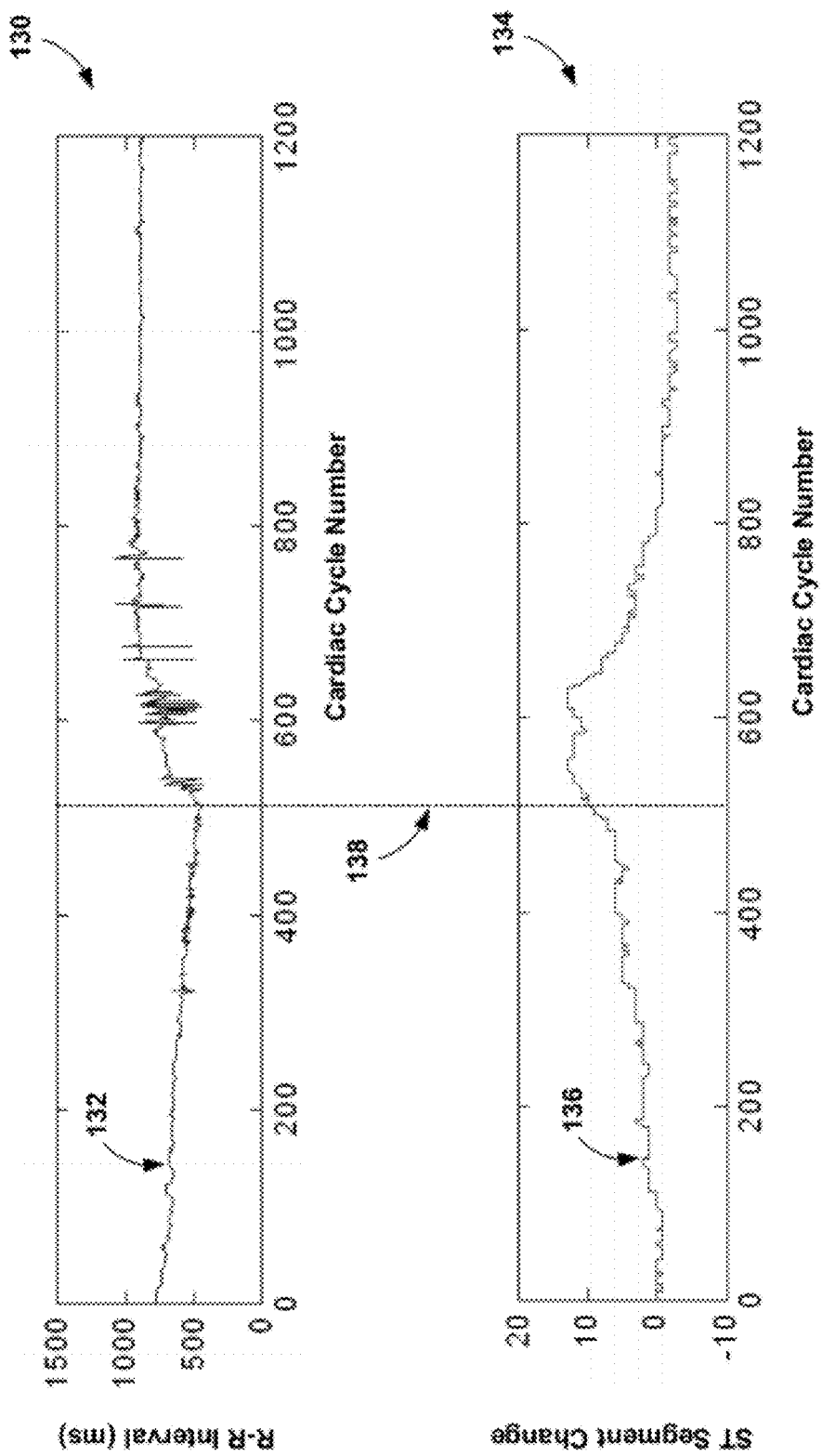
FIG. 6 illustrates an example electrogram that includes sample R-R interval and ST segment changes over consecutive cardiac cycles.

FIG. 6 illustrates an example electrogram that includes sample R-R interval graph 130 and ST segment change graph 134 in which ST segment changes follow increases in heart rate. As shown in FIG. 6, endocardial and non-endocardial electrograms may be processed so that certain aspects of the electrogram can be analyzed. For example, an electrogram may be processed so that the R-R interval, or length of each cardiac cycle, can be identified in R-R interval graph 130. Interval data 132 indicates the interval length between each cardiac cycle because IMD 16 has detected each R wave during the electrogram. Therefore, shorter R-R intervals indicate an increased heart rate. The lowest R-R interval of FIG. 6 is approximately 500 ms in length and correlates to the maximum heart rate indicated by marker 138.

The maximum heart rate of marker 138 occurs before the maximum ST segment change. R-R interval graph 130 is matched for each cardiac cycle to ST segment change graph 134. In ST segment change graph 134, segment data 136 is generated by comparing the ST segment amplitude to the amplitude of the QRS complex. Therefore, the ST segment change is indicated as a percentage of the QRS amplitude. In other examples, the ST segment amplitude may be a raw amplitude not normalized to the QRS complex amplitude. In the example of FIG. 6, segment data 136 indicates a change in ST segments that lags behind the increase in heart rate indicated by interval data 132. Segment data 136 increases as interval data 132 decreases, but the maximum ST segment change does not occur until after the maximum heart rate indicated by marker 138.

In the example of FIG. 6, ischemia detection module 83 may detect ischemia if the predetermined threshold is set to 10 percent of the QRS amplitude because segment data 136 indicates that the ST segment change approaches 13 percent of the QRS amplitude. As the heart rate declines in subsequent cardiac cycles, the ST segment change comes back to baseline because the ischemic conditions have dissipated. In this manner, ischemia detection module 83 may detect ischemia by monitoring data similar to that of segment data 136. Although FIG. 6 provides a comparison between R-R intervals and a change in ST segments, IMD 16 may not perform this direct comparison in order to detect and classify types of ischemia.

Although the ST segment change is detected based on the predetermined threshold as a percentage of the QRS complex amplitude, the predetermined threshold may be set to another set of data. As described herein, the predetermined threshold may be a percentage of a QRS complex amplitude, a voltage threshold, an ST segment change relative to the baseline variability of the ST segment, or some other criteria. For example, ischemia detection module 83 may detect the ST segment change indicative of ischemia when the rate of ST segment change exceeds a threshold. Monitoring the rate of ST segment change may be beneficial because slow changes with patient condition or sensing drift may not affect the ability of ischemia detection module 83 to accurately detect the presence of ischemia. In various examples, any type of threshold or criteria may be implemented to determine when a ST segment change indicates ischemia.

Figure 7:
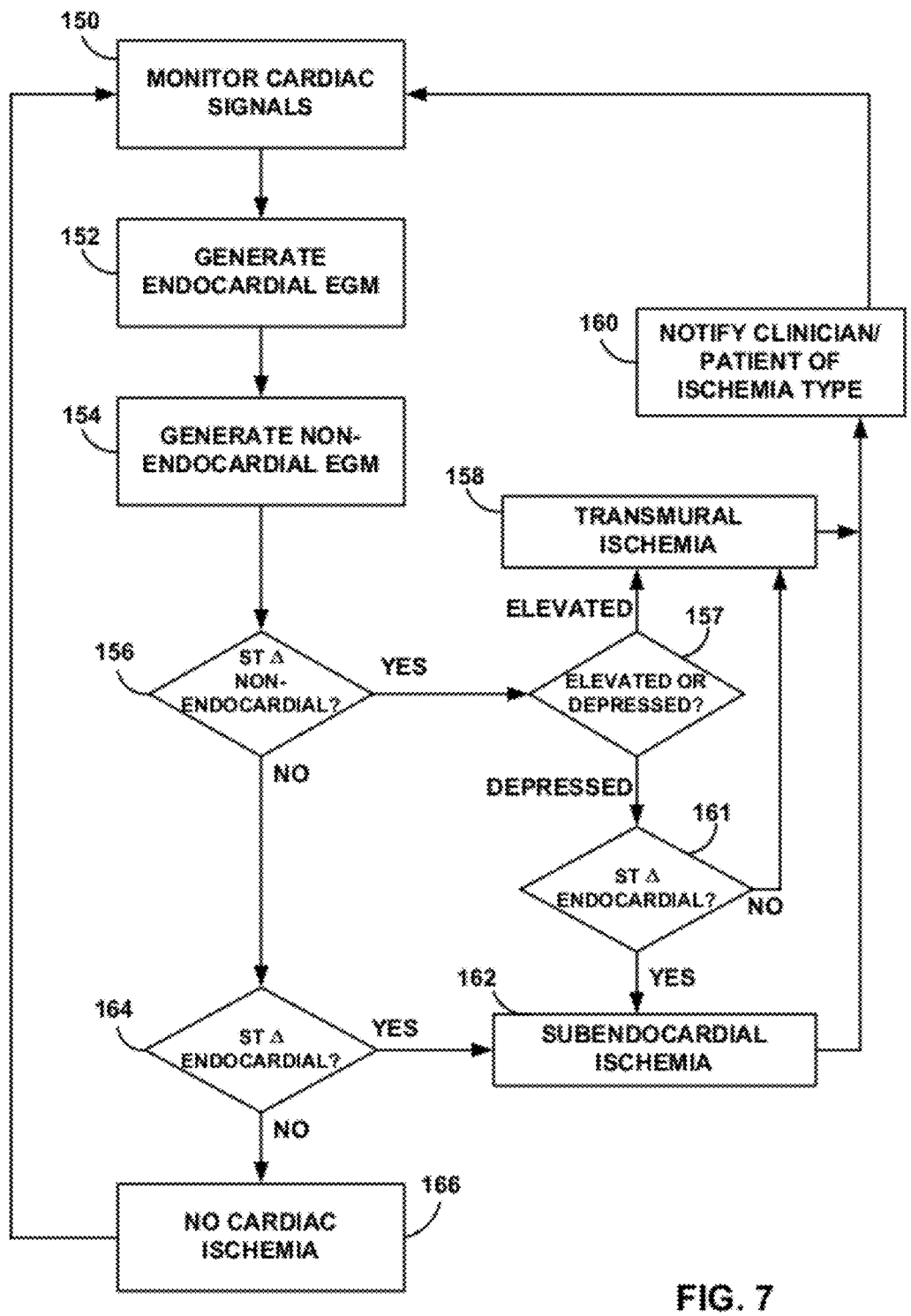
FIG. 7 is a flow diagram of an example method for detecting and classifying ischemia from multiple electrograms.

FIG. 7 is a flow diagram of an example method for detecting and classifying ischemia from multiple electrograms. FIG. 7 is described using processor 80 and ischemia detection module 83 of IMD 16, but other processors, modules, or devices may be used to implement these example techniques. In the example of FIG. 7, sensing module 86 monitors cardiac electrical signals from heart 12 (150). Processor 80 then generates an endocardial electrogram (EGM) from an endocardial electrode vector (152) and generates a non-endocardial electrogram from an epicardial electrode vector (154). As described herein, the electrode vectors include electrodes implanted within patient 14, and both the endocardial and non-endocardial electrograms are generated for the same time period (e.g., simultaneous cardiac cycles).

Ischemia detection module 83 then analyzes the endocardial and non-endocardial electrograms for changes in the ST segments. If ischemia detection module 83 detects an ST segment change in the non-endocardial electrogram ("YES" branch of block 156), then ischemia detection module 83 has detected ischemia and further determines whether the ST segment is elevated or depressed (157). If the ST segment is elevated, ischemia detection module classifies the ischemia as a malignant ischemia, e.g., a transmural ischemia in the example of FIG. 7 (158). Processor 80 may then notify the clinician and/or patient of the malignant ischemia (160). Since transmural ischemia is a severe condition for patient 14, the notification or alert may be pushed to programmer 24 or another external computing device so that patient 14 receives treatment for the ischemic condition.

On the other hand, if ischemia detection module 83 determines that the ST segment is depressed, ischemia detection module 83 further determines whether a change in the ST segment of the endocardial electrogram has occurred (161). If ischemia detection module 83 determines that no change to the ST segment of the endocardial electrogram has occurred, ischemia detection module 83 classifies the ischemia as malignant, e.g., transmural (158) and notifies the clinician or patient (160). If ischemia detection module 83 detects a change in the ST segment of the endocardial electrogram coincident with the change in the non-endocardial electrogram ("YES" branch of 161), ischemia detection module 83 classifies the ischemia as a benign ischemia, e.g., subendocardial ischemia in the example of FIG. 7 (162), and notifies the clinician or patient (160). Since subendocardial ischemia is not very severe, the notification or alert may only be presented by programmer 24 the next time communication occurs between programmer 24 and IMD 16.

It is noted that detecting or not detecting a change in the endocardial electrogram (161) may comprise determining whether a change occurs in the endocardial electrogram coincident with or sufficiently proximate to, e.g., within a time interval of, the change in the non-endocardial electrogram. In other words, in some cases, ischemia detection module 83 may determine that no change occurred in the endocardial electrogram although a change may, in fact, later occur.

If ischemia detection module 83 does not detect a change in the non-endocardial electrogram ("NO" branch of 156), but does detect a change in the endocardial electrogram ("YES" branch of 164), ischemia detection module 83 detects an ischemia and classifies it as a benign ischemia, e.g., a subendocardial ischemia in the example of FIG. 7 (162). Processor 80 may then notify the clinician/patient (160), and the processor and sensing module 86 may continue to monitor cardiac signals (150). It is noted that in some examples, ST segment changes in a non-endocardial electrogram may still occur during a benign ischemia, e.g., subendocardial ischemia, but at a later time than those ST segment changes in the endocardial electrogram indicating the benign ischemia.

If ischemia detection module 83 does not detect ST segment changes in either non-endocardial or endocardial electrogram ("NO" branch of block 164), ischemia detection module 83 indicates that no cardiac ischemia is present (166). Processor 80 and sensing module 86 then continue to monitor cardiac signals (150). In other examples, ischemia detection module 83 may monitor only one electrogram or more than two electrograms. Therefore, ischemia detection module 83 may be able to detect ischemia localized near other electrodes or compensate for malfunctioning electrode vectors.

In one example, processor 80 may also detect a substantial increase in heart rate after the detected ST segment change. This heart rate increase may be indicative of a severe ischemic episode. Therefore, processor 80 may identify the severe ischemic episode and push an alert to patient 14 or programmer 24 (e.g., a visual, audible, or tactile indication) or initiate therapeutic remedies.

Figure 8:
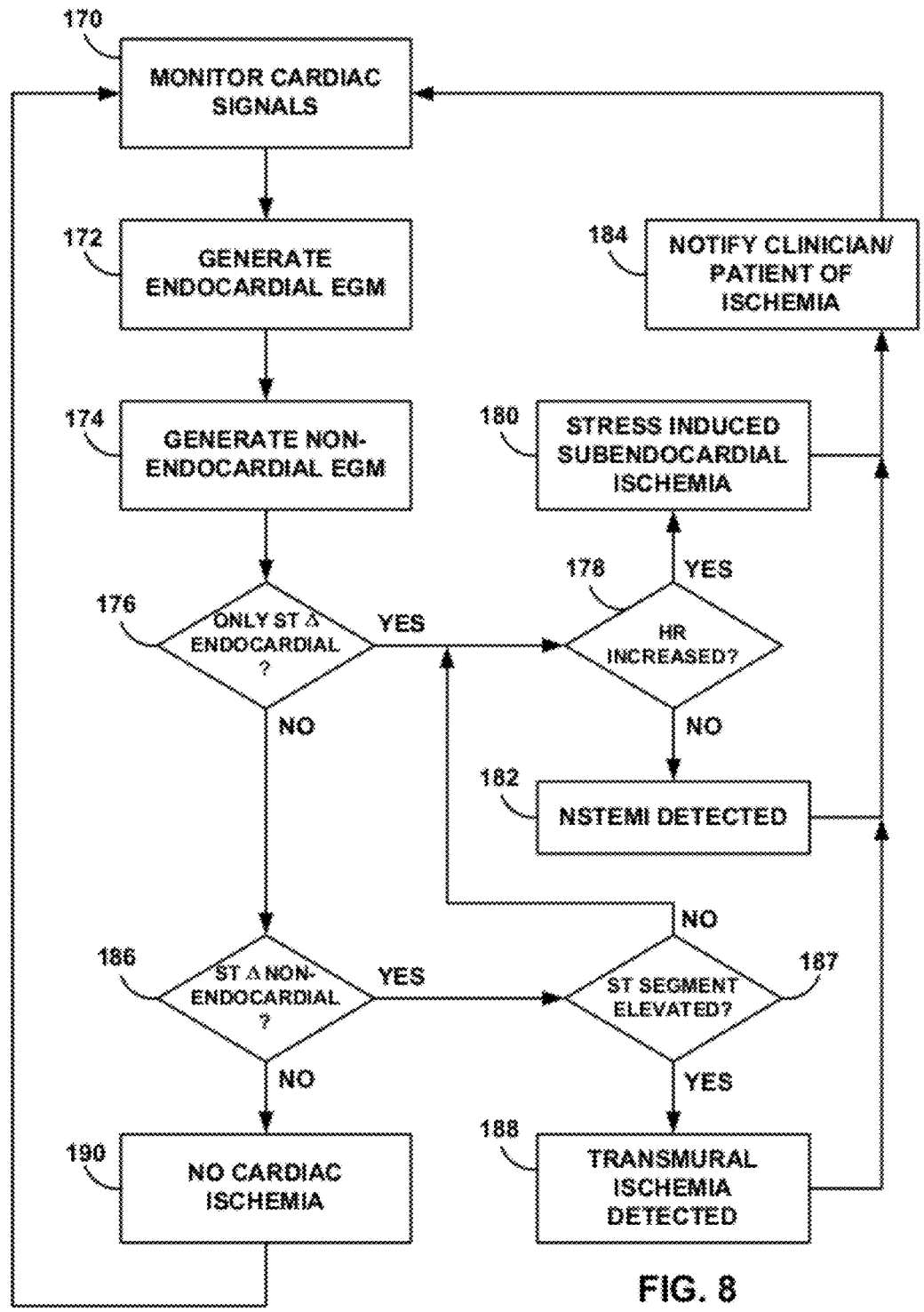
FIG. 8 is a flow diagram of an example method for classifying ischemia with ST segment changes and heart rate data.

FIG. 8 is a flow diagram of an example method for classifying ischemia with ST segment changes and heart rate data. FIG. 8 may be similar to FIG. 7, but the technique of FIG. 8 may also implement heart rate monitoring to further differentiate and classify types of ischemia. In other examples, patient activity levels may be monitored instead of, or in addition to, the heart rate of patient 14 to further classify types of ischemia.

In the example of FIG. 8, sensing module 86 monitors cardiac electrical signals from heart 12 (170). Processor 80 then generates an endocardial electrogram (EGM) from an endocardial electrode vector (172) and generates a non-endocardial electrogram from an epicardial electrode vector (174). As described herein, the electrode vectors include electrodes implanted within patient 14, and both the endocardial and non-endocardial electrograms are generated for the same time period (e.g., simultaneous cardiac cycles).

Ischemia detection module 83 then analyzes the endocardial and non-endocardial electrograms for changes in the ST segments (176). If ischemia detection module 83 only detects an ST segment change in the endocardial electrogram ("YES" branch of block 176), ischemia detection module 83 then analyzes the heart rate of patient 14 during the now detected ischemic condition. If the heart rate has increased substantially over the baseline heart rate ("YES" branch of block 178), then ischemia detection module 83 classifies the ischemia type as stress induced subendocardial ischemia (180). If the heart rate has stayed substantially constant during the ischemic condition ("NO" branch of block 178), then ischemia detection module 83 classifies the ischemia type as a non-ST elevation myocardial infarction (NSTEMI) (182). In other examples, the timing of the heart rate increase with respect to the detected ischemia may be determined. Since heart rate elevation in response to ischemia is more problematic to the health of patient 14, heart rate increases occurring after the ischemia is detected may trigger more immediate notification of patient 14 and/or a clinician. As indicated above, it is noted that in some examples, ST segment changes in a non-endocardial electrogram may still occur at a later time than those ST segment changes in the endocardial electrogram indicating subendocardial ischemia.

To determine if the heart rate has increased substantially or remained substantially constant during the ischemic condition, one or more thresholds may be implemented. In one example, a stress threshold may be used such that a substantially increased heart rate may have a heart rate exceeding the stress threshold. An example stress threshold may be 100 beats per minute, but other examples may have stress thresholds between approximately 70 beats per minute and 160 beats per minute. Alternatively, the stress threshold may be a moving threshold that is a percentage of the baseline heart rate or responsive to other patient conditions.

After ischemia detection module 83 has classified the type of detected ischemia, processor 80 may then notify the clinician and/or patient of the type of ischemia (184). Stress induced subendocardial ischemia may be a less severe type of ischemia because coronary artery occlusions are only a problem when blood supply is in higher demand. Therefore, this notification or alert may only be presented by programmer 24 the next time communication occurs between programmer 24 and IMD 16. However, NSTEMI classification may require more immediate intervention. In this case, processor 80 may push the notification or alert to programmer 24 or another external computing device so that patient 14 receives treatment. Processor 80 and sensing module 86 then continue to monitor cardiac signals (170).

If ischemia detection module 83 detects an ST segment change in the endocardial electrogram and the non-endocardial electrogram ("YES" branch of block 186), then ischemia detection module 83 has detected ischemia and checks whether the ST segment change is ST segment change elevation or depression. If the ST segment is elevated ("YES" branch of block 187), then ischemia detection module 83 classifies the ischemia as transmural ischemia (188). If the ST segment is depressed ("NO" branch of block 187), then ischemia detection module 83 checks for heart rate increases prior to classifying the ischemia (178). As mentioned above, a depressed ST segment change may still be indicative of transmural ischemia in some examples. In this case, further patient examination may be performed. In some examples, the ST segment changes detected in both endocardial and non-endocardial electrograms may not occur at the same time. However, ischemia detection module 83 may still detect the ST segment change in both electrograms given this time delay.

Processor 80 may then notify the clinician and/or patient of the transmural ischemia (184). The notification or alert may be pushed to programmer 24 or another external computing device so that patient 14 receives treatment for this more severe ischemic condition. Processor 80 and sensing module 86 may then continue to monitor cardiac signals (170). Although ischemia detection module 83 may detect the ST change in both the endocardial and non-endocardial electrograms to classify the ischemia as transmural, ischemia detection module 83 may classify the ischemia as transmural ischemia based only on the non-endocardial electrogram in other examples.

If ischemia detection module 83 does not detect ST segment changes in either non-endocardial or endocardial electrogram ("NO" branch of block 186), ischemia detection module 83 indicates that no cardiac ischemia is present (190). Processor 80 and sensing module 86 then continue to monitor cardiac signals (150). In other examples, ischemia detection module 83 may monitor only on electrogram or more than two electrograms. Therefore, ischemia detection module 83 may be able to detect ischemia localized near other electrodes or compensate for malfunctioning electrode vectors.

Figure 9:
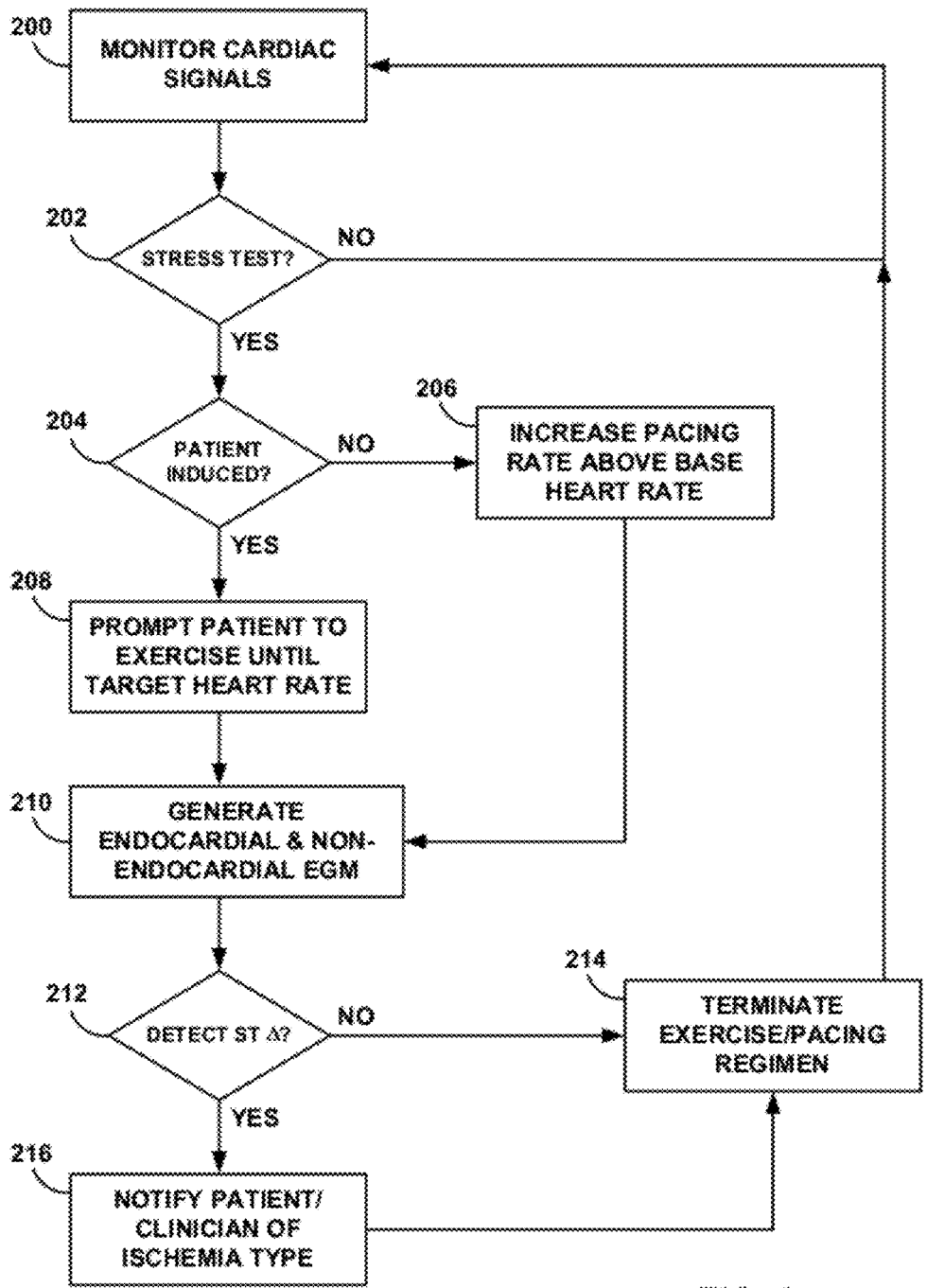
FIG. 9 is a flow diagram of an example method for conducting a stress test and classifying any resulting ischemia by detecting ST segment changes.

FIG. 9 is a flow diagram of an example method for conducting a stress test and classifying any resulting ischemia by detecting ST segment changes. FIG. 9 is described using IMD 16 and programmer 24, but other devices may also be used to implement these example techniques. In the example of FIG. 9, sensing module 86 monitors cardiac electrical signals from heart 12 (200). If processor 80 does not determine that a stress test should be completed ("NO" branch of block 204), then IMD 16 continues to monitor cardiac signals of heart 12 (200). Processor 80 may determine that a stress test is required based upon a schedule stored in memory 82, an instruction from programmer 24 or other device, or certain patient conditions detected by processor 80. If processor 80 determines that a stress test needs to occur ("YES" branch of block 202), the processor 80 determines if the stress test should be patient induced (204).

If the stress test is not to be patient induced ("NO" branch of block 204), then processor automatically increases the pacing rate above the base or normal heart rate (206). Generally, atrial pacing may be used to perform this automated stress test with IMD 16 to keep the intrinsic QRS complex intact and maintain easier detection of ischemia. However, other pacing methods may also be used, e.g., ventricular pacing. This process may be considered an artificial stress test because IMD 16 creates oxygen demand at heart 12 by forcing the heart to beat faster. If the stress test is to be patient induced ("YES" branch of block 204), then processor 80 prompts patient 14 via user interface 104 to exercise until the target heart rate is reached (208).

Once the heart rate begins to increase, processor 80 generates an endocardial electrogram and a non-endocardial electrogram with an endocardial electrode vector and an epicardial electrode vector, respectively (210). If ischemia detection module 83 detects ischemia through changes in ST segments as described in FIGS. 7 and 8 ("YES" branch of block 216), processor 80 notifies the patient and/or clinician via user interface 104 of the type of ischemia detected during the stress test (216). If ischemia detection module 83 does not detect changes in ST segments indicative of ischemia ("NO" branch of block 212), processor 80 terminates the exercising or pacing regimen of the stress test (214). Processor 80 may then continue to monitor cardiac signals.

In some examples, processor 80 may initiate this stress test technique automatically when the heart rate of patient 14 exceeds a certain threshold. In this manner, processor 80 may avoid a separate stress test event. In other examples, processor 80 may store the electrograms and/or other data related to the stress test in memory 82 of IMD 16 or memory 102 of programmer 24. The clinician may desire to review the stress test data to look for other abnormalities if there was no ischemia detected or confirm the presence of ischemia if it was detected. User interface 104 may present this stress data, but other examples may include another external computing device to present the stress data.

Although transmural ischemia, subendocardial ischemia, and non ST elevation myocardial infarction are described herein as types of ischemia detected and classified by the above mentioned techniques, these three types of ischemia are used as general examples of types of benign and malignant ischemia. Non-ST elevation myocardial infarction and transmural ischemia may generally be referred to as types of malignant ischemia. Subendocardial ischemia may be a type of benign ischemia. In other words, the techniques herein may generally apply to the differentiation between more severe types of ischemia, e.g., transmural ischemia, and less severe types of ischemia, e.g., subendocardial ischemia.

The techniques described herein allow an IMD to monitor cardiac rhythms and automatically detect and classify different types of ischemia with implanted electrodes. The use of endocardial electrograms from endocardial electrode vectors may allow for the detection of localized subendocardial ischemia not detectable with non-endocardial electrograms. However, non-endocardial electrograms from epicardial electrode vectors may also allow for the detection of transmural ischemia. Heart rate information may also allow the ischemia to be differentiated on the basis of stress to the heart. Further, these techniques may be used to perform more sensitive stress testing of patient with IMDs than could otherwise be performed with surface electrodes. Therefore, the techniques described herein may allow for earlier detection of ischemia and treatment of the patient that may preempt tissue damage at a later time.

Various examples have been described that include detecting and classifying, e.g., diagnosing, types of ischemia from electrograms and cardiac rhythms. These examples include techniques for differentiating subendocardial ischemia from transmural ischemia. In addition, an alert or notification may be delivered and presented to a user to indicate that the patient has suffered an ischemic condition. Any combination of detection and classification of ischemia is contemplated. These and other examples are within the scope of the following claims.

The invention claimed is:

1. A system comprising:
a first electrode and a second electrode both implanted within a heart of a patient;
a third electrode outside of the heart;
a processor configured to generate an endocardial electrogram of the heart with an endocardial electrode vector between the first electrode and the second electrode during a time period and generate a non-endocardial electrogram of the heart with an epicardial electrode vector comprising the third electrode during the time period; and
an ischemia detection module configured to detect a change in at least one electrogram metric of at least one of the non-endocardial electrogram or the endocardial electrogram, and classify an ischemia of the heart during the time period as one of a plurality of ischemia types based on the detection.

2. The system of claim 1, wherein the ischemia detection module is configured to detect a change in an ST segment of at least one of the non-endocardial electrogram or the endocardial electrogram, and classify the ischemia based on the detection of the change of the ST segment.

3. The system of claim 1, wherein the ischemia detection module is configured to classify the ischemia as one of a plurality of severities based on the detection.

4. The system of claim 1, wherein the ischemia detection module classifies the ischemia as a subendocardial ischemia when the electrogram metric change is detected only in the endocardial electrogram during the time period.

5. The system of claim 4, wherein the ischemia detection module:
detects an increase in at least one of a heart rate or an activity level of the patient during or before the detected electrogram metric change; and
classifies the ischemia type as a stress induced subendocardial ischemia based on the detection of the increase in the at least one of the heart rate or the activity level.

6. The system of claim 1, wherein the ischemia detection module:
detects an increase in at least one of a heart rate or an activity level of the patient after the detected electrogram metric change; and
classifies the ischemia as malignant based on the detection of the increase in heart rate after the detected electrogram metric change.

7. The system of claim 1, wherein the ischemia detection module detects ST segment elevation in the non-endocardial electrogram, and classifies the ischemia as a transmural ischemia based on the detection of the T segment elevation in the non-endocardial electrogram.

8. The system of claim 1, further comprising a user interface of an external computing device, wherein:
the ischemia detection module, based on the ischemia type, automatically transmits at least one of a notification to a healthcare professional of the ischemia type and an instruction to the patient to seek medical treatment; and
the user interface presents the at least one of the notification to the healthcare professional of the ischemia type and the instruction to the patient to seek medical treatment.

9. The system of claim 1, wherein the processor at least one of generates an instruction to be presented to the patient to induce an increase in heart rate via exercise or increases a pacing rate to artificially induce the increase in heart rate.

10. The system of claim 1, further comprising:
a first lead comprising the first electrode and the second electrode, wherein the first electrode is a tip electrode located at a distal end of the first lead and configured to contact cardiac tissue and the second electrode is a ring electrode located proximal to the tip electrode; and
an implantable medical device housing comprising the third electrode.

11. The system of claim 10, further comprising a fourth electrode outside of the heart, wherein one of the third electrode and the fourth electrode is coupled to an implantable medical device housing, the fourth electrode is an external surface electrode, or the third electrode and the fourth electrode are carried on a lead implanted within a coronary sinus of the heart.

12. The system of claim 1, further comprising an implantable medical device coupled to the electrodes that comprises the processor and the ischemia detection module.

13. A system comprising:
means for generating a endocardial electrogram of a heart with an endocardial electrode vector within a patient during a time period and generating a non-endocardial electrogram of the heart with an epicardial electrode vector during the time period;
means for detecting a change in at least one electrogram metric of at least one of the non-endocardial electrogram or the endocardial electrogram; and
means for classifying an ischemia of the heart during the time period as one of a plurality of ischemia types based on the detection.

14. The system of claim 13,
wherein the means for detecting a change in at least one electrogram metric comprises means for detecting a change in an ST segment of the electrogram, and
wherein the means for classifying the ischemia:
classifies the ischemia as a subendocardial ischemia when the ST segment change is detected only in the endocardial electrogram; and
classifies the ischemia as a transmural ischemia when an ST segment elevation is detected in the non-endocardial electrogram.

15. The system of claim 1, wherein the ischemia detection module is configured to monitor both of the endocardial electrogram and the non-endocardial electrogram for a change to at least one electrogram metric of at least one of the non-endocardial electrogram or the endocardial electrogram.

16. A method comprising:
generating, by a processor, a endocardial electrogram of a heart during a period of time with an endocardial electrode vector between a first electrode implanted within the heart and a second electrode implanted within the heart;
generating, by the processor, a non-endocardial electrogram of the heart during the period of time with an epicardial electrode vector comprising a third electrode outside of the heart;
detecting, by an ischemia detection module, a change in at least one electrogram metric of at least one of the non-endocardial electrogram or the endocardial electrogram; and
classifying, by the ischemia detection module, an ischemia of the heart during the time period as one of a plurality of ischemia types based on the detection.

17. The method of claim 16, wherein detecting a change in an electrogram metric comprises detecting a change in an ST segment of the electrogram.

18. The method of claim 16, wherein classifying the ischemia of the heart during the time period comprises classifying the ischemia as one of a plurality of severities based on the detection.

19. The method of claim 16, wherein classifying the ischemia further comprises classifying the ischemia as a subendocardial ischemia when the electrogram metric change is detected only in the endocardial electrogram during the time period.

20. The method of claim 19, further comprising:
detecting an increase in at least one of a heart rate or an activity level of the patient during or before the detected electrogram metric change; and
classifying the ischemia type as a stress induced subendocardial ischemia based on the detection of the increase in the at least one of the heart rate or the activity level.

21. The method of claim 16, further comprising:
detecting an increase in at least one of a heart rate or an activity level of the patient after the detected electrogram metric change; and
classifying the ischemia as malignant based on the detection of the increase in heart rate after the detected electrogram metric change.

22. The method of claim 16, wherein detecting a change in at least one electrogram metric comprises detecting ST segment elevation in the non-endocardial electrogram, and wherein classifying the ischemia comprises classifying the ischemia as a transmural ischemia based on the detection of the ST segment elevation in the non-endocardial electrogram.

23. The method of claim 16, further comprising, based on the ischemia type, at least one of automatically notifying a healthcare professional of the ischemia type and automatically instructing the patient to seek medical treatment via an external computing device.

24. The method of claim 16, further comprising one of presenting an instruction to the patient to induce an increase in heart rate via exercise or increasing a pacing rate to artificially induce the increase in heart rate.

* * * * *